United States Patent
Ukai et al.

(10) Patent No.: US 9,573,061 B2
(45) Date of Patent: *Feb. 21, 2017

(54) VIDEO GAME WITH AUTOMATIC COMBINATION OR SELLING OF ACQUIRED ITEMS

(71) Applicant: DeNA Co., Ltd., Tokyo (JP)

(72) Inventors: Yuji Ukai, Tokyo (JP); Naoto Yoshie, Tokyo (JP); Tomoyuki Ono, Tokyo (JP)

(73) Assignee: DeNA Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/973,462

(22) Filed: Dec. 17, 2015

(65) Prior Publication Data
US 2016/0104349 A1    Apr. 14, 2016

Related U.S. Application Data

(63) Continuation of application No. 14/261,726, filed on Apr. 25, 2014, now Pat. No. 9,241,836, which is a
(Continued)

(30) Foreign Application Priority Data

Aug. 24, 2012   (JP) .................................. 2012-185605

(51) Int. Cl.
*A63F 13/00* (2014.01)
*A63F 13/45* (2014.01)
(Continued)

(52) U.S. Cl.
CPC ............... *A63F 13/45* (2014.09); *A61F 13/10* (2013.01); *A63F 13/00* (2013.01); *A63F 13/12* (2013.01);
(Continued)

(58) Field of Classification Search
CPC .......... A63F 13/10; A63F 13/60; A63F 13/69; A63F 13/79
See application file for complete search history.

(56) References Cited

U.S. PATENT DOCUMENTS

2002/0155893 A1    10/2002    Swanberg et al.

FOREIGN PATENT DOCUMENTS

JP        2008-264183 A    11/2008

OTHER PUBLICATIONS

Japanese Office Action issued in related Japanese Patent Application No. 2013-044520 on Sep. 24, 2013, 5 pages.
(Continued)

*Primary Examiner* — Lawrence Galka
(74) *Attorney, Agent, or Firm* — Rothwell, Figg, Ernst & Manbeck, P.C.

(57) ABSTRACT

The game program according to the present invention causes a computer to perform a registering process to register in advance in a storage unit attribute information specified by the player, an offering process to offer the game content to the player, a judgment process to compare the attribute information of the game content offered to the specified attribute information, a combining process to combine the game content offered with another game content to create a combined game content, and a recording process to record in the storage unit the combined game content as the game content owned by the player, without recording in the storage unit the game content offered as the game content owned by the player.

5 Claims, 14 Drawing Sheets

Related U.S. Application Data continuation of application No. 13/905,970, filed on May 30, 2013, now Pat. No. 8,747,202.

(51) Int. Cl.
*A63F 13/69* (2014.01)
*A63F 13/60* (2014.01)
*A63F 13/95* (2014.01)
*A61F 13/10* (2006.01)
*A63F 13/30* (2014.01)
*A63F 13/355* (2014.01)
*A63F 13/79* (2014.01)
*G07F 17/32* (2006.01)

(52) U.S. Cl.
CPC .............. *A63F 13/355* (2014.09); *A63F 13/60* (2014.09); *A63F 13/69* (2014.09); *A63F 13/79* (2014.09); *A63F 13/95* (2014.09); *G07F 17/3241* (2013.01); *G07F 17/3255* (2013.01); *G07F 17/3272* (2013.01); *A63F 2300/5546* (2013.01); *A63F 2300/6054* (2013.01)

(56) References Cited

OTHER PUBLICATIONS

Bahamut Brave, Appli Style vol. 5, Eastpress Corporation, Nov. 15, 2011, Koiunreki November special edition, p. 041, 5 pages.
Crows x Worst Saikyodensentsu, Appli Style vol. 5, Eastpress Corporation, Nov. 15, 2011, Koiunreki November special edition, pp. 029-031, 7 pages.

| CARD ID | CHARACTER NAME | CHARACTER IMAGE | RARITY | INITIAL (LV.1) ATTACK POWER | INITIAL (LV.1) DEFENSE POWER |
|---|---|---|---|---|---|
| 0001 | WARRIOR A | 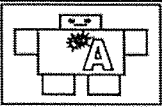 | COMMON | 15 | 8 |
| 0002 | WARRIOR A | 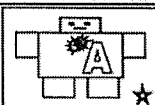 | UNCOMMON | 20 | 15 |
| 0003 | WARRIOR A | 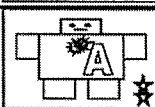 | RARE | 100 | 60 |
| 0004 | WARRIOR A | 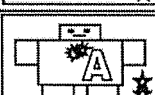 | SUPER RARE | 200 | 180 |
| 0011 | WARRIOR B |  | COMMON | 10 | 5 |
| 0012 | WARRIOR B | 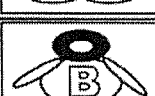 | UNCOMMON | 15 | 10 |
| 0013 | WARRIOR B | 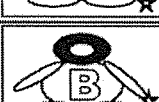 | RARE | 80 | 50 |
| ⋮ | ⋮ | ⋮ | ⋮ | ⋮ | ⋮ |
| 2591 | WIZARD Z |  | COMMON | 20 | 30 |
| 2592 | WIZARD Z |  | UNCOMMON | 50 | 75 |
| 2593 | WIZARD Z |  | RARE | 60 | 100 |
| 2594 | WIZARD Z |  | SUPER RARE | 150 | 300 |
FIG. 4

| PLAYER ID | FRIEND PLAYER ID | VIRTUAL CURRENCY | PLAY POINT | OWNED CARD INFORMATION | PICTORIAL BOOK INFORMATION |
|---|---|---|---|---|---|
| 1 | 5, 8 | 0 | 15000 | OWNED CARD INFORMATION (1) | PICTORIAL BOOK INFORMATION (1) |
| 2 | NONE | 500 | 6000 | OWNED CARD INFORMATION (2) | PICTORIAL BOOK INFORMATION (2) |
| 3 | 4, 6 | 700 | 50000 | OWNED CARD INFORMATION (3) | PICTORIAL BOOK INFORMATION (3) |
| 4 | 3, 6 | 1000 | 90000 | OWNED CARD INFORMATION (4) | PICTORIAL BOOK INFORMATION (4) |
| 5 | 1, 6 | 100 | 40000 | OWNED CARD INFORMATION (5) | PICTORIAL BOOK INFORMATION (5) |
| 6 | 3, 4, 5 | 3000 | 30000 | OWNED CARD INFORMATION (6) | PICTORIAL BOOK INFORMATION (6) |
| ⁝ | ⁝ | ⁝ | ⁝ | ⁝ | ⁝ |

| OWNED CARD INFORMATION (1) | | | | |
|---|---|---|---|---|
| OWNED CARD ID | LEVEL | ATTACK POWER | DEFENSE POWER | ACQUISITION DATE/TIME |
| 0011 | LV. 3 | 15 | 10 | 2012/2/13 10:00 |
| 0211 | LV. 4 | 20 | 23 | 2012/2/13 12:00 |
| 0133 | LV. 1 | 70 | 45 | 2012/2/14 11:30 |
| 0201 | LV. 4 | 22 | 40 | 2012/2/15 18:00 |
| 0072 | LV. 7 | 60 | 50 | 2012/2/16 13:30 |
| 0094 | LV. 1 | 300 | 200 | 2012/2/16 19:00 |
| ... | ... | ... | ... | ... |

| PICTORIAL BOOK INFORMATION (1) ||
|---|---|
| CARD ID | FLAG SHOWN |
| 0001 | TRUE |
| 0002 | FALSE |
| 0003 | FALSE |
| 0004 | FALSE |
| 0011 | TRUE |
| 0012 | TRUE |
| . | . |
| . | . |
| . | . |

FIG. 7

VIDEO GAME WITH AUTOMATIC COMBINATION OR SELLING OF ACQUIRED ITEMS

CROSS-REFERENCE TO RELATED APPLICATIONS

This application is a continuation of U.S. application Ser. No. 14/261,726, filed Apr. 25, 2014, which is a continuation of U.S. application Ser. No. 13/905,970, filed May 30, 2013, now U.S. Pat. No. 8,747,202, which claims priority upon Japanese Patent Application No. 2012-185605 filed on Aug. 24, 2012. The disclosure of each of the above-referenced applications are which is herein incorporated by reference in their entirety.

BACKGROUND

Technical Field

This invention relates to a non-transitory computer-readable storage medium and an information processing device.

Related Art

A game system is known that executes a game in which a player uses a game content such as character cards (for example, see Japanese Laid-Open Patent Publication No. 2008-264183).

In such a game system, game contents used in a game are offered to a player. Here, when game contents are offered to the player one after another, the player will own a large number of game contents. However, since there is a limit to the number of game contents that can be owned to the player, the player needs to judge whether or not the player needs the offered game contents taking into consideration the number of game contents owned and take the time and effort to perform a manipulated input according to the necessity or unnecessity thereof.

SUMMARY

The present invention has been conceived in view of the above issue, and an object thereof is to relieve the time and effort required for the manipulated input.

An aspect of the invention to solve the above and other problems is a non-transitory computer-readable storage medium storing a game program for causing a computer including a processor and a memory to execute a game in which a player uses a game content to which attribute information is set, the game program instructing the computer to perform the following processes of a registering process to register in advance in a storage unit attribute information specified by the player;

an offering process to offer the game content to the player;

a judgment process to compare the attribute information of the game content offered to the specified attribute information, and judge whether or not the game content offered is to be made the game content owned by the player;

a combining process to combine the game content offered with an other game content to create a combined game content when the game content offered is judged not to be made the game content owned by the player; and a recording process to record in the storage unit the combined game content as the game content owned by the player, without recording in the storage unit the game content offered as the game content owned by the player.

Other features of the present invention will become apparent from the description in the detailed description of the invention and the attached drawings.

BRIEF DESCRIPTION OF DRAWINGS

FIG. 4 illustrates an example of a data structure of card information.

FIG. 5 illustrates an example of a data structure of player information.

FIG. 6 illustrates an example of a data structure of owned card information.

FIG. 7 illustrates an example of a data structure of pictorial book information.

DETAILED DESCRIPTION OF THE INVENTION

Figure 1:
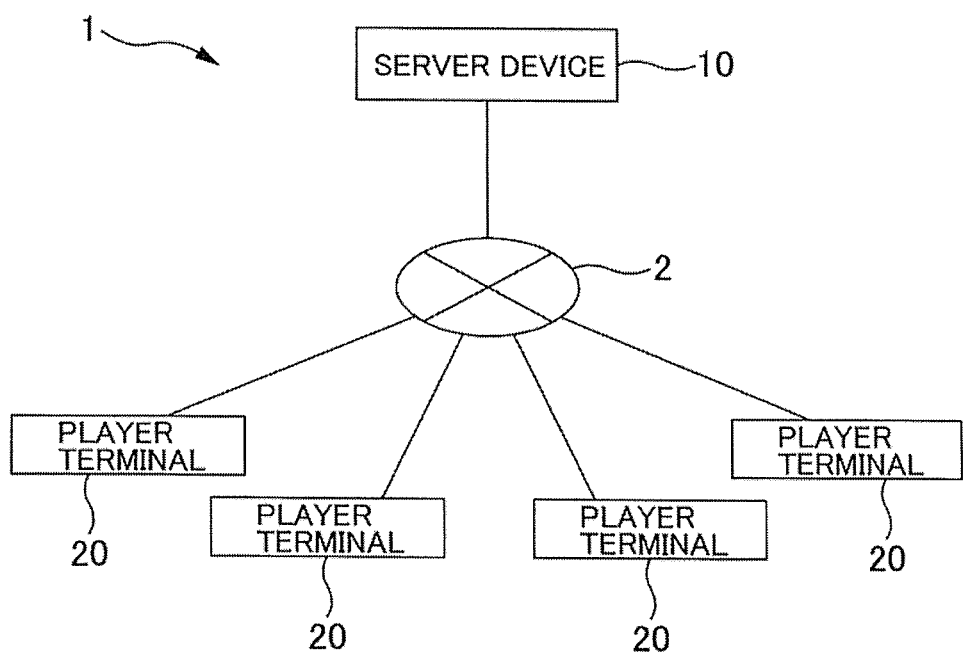
FIG. 1 illustrates an example of an overall configuration of a game system 1.

From the description in the detailed description of the invention and the accompanied drawings, at least the following matters will be apparent.

In other words, a non-transitory computer-readable storage medium storing a game program for causing a computer including a processor and a memory to execute a game in which a player uses a game content to which attribute information is set, the game program instructing the computer to perform the following processes of a registering process to register in advance in a storage unit attribute information specified by the player;

an offering process to offer the game content to the player;

a judgment process to compare the attribute information of the game content offered to the specified attribute information, and judge whether or not the game content offered is to be made the game content owned by the player;

a combining process to combine the game content offered with an other game content to create a combined game content when the game content offered is judged not to be made the game content owned by the player; and a recording process to record in the storage unit the combined game content as the game content owned by the player, without recording in the storage unit the game content offered as the game content owned by the player.

According to such a game program, since the game content after automatic composition is owned by the player, the time and effort for performing a manipulated input can be saved.

Further, the computer-readable storage medium storing a game program, wherein the game program instructs the computer to perform in the registering process, registering in the storage unit in advance an other game content specified by the player;

in the combining process, combining the game content offered with the other game content specified, when the game content offered is judged not to be made the game content owned by the player;

in the recording process, recording in the storage unit an other combined game content as the game content owned by the player.

According to such a game program, since the other game content after automatic composition is owned by the player, the time and effort for performing a manipulated input can be saved.

Further, the computer-readable storage medium storing a game program, wherein the game program instructs the computer to perform in the combining process, automatically selecting an other game content and combining the game content offered with the selected other game content when the game content offered is judged not to be made the game content owned by the player; and in the recording process, recording in the storage unit an other combined game content as the game content owned by the player.

According to such a game program, since the other game content is selected automatically and the other game content after automatic composition is owned by the player, the time and effort for performing a manipulated input can be saved.

Further, the computer-readable storage medium storing a game program, wherein the game program instructs the computer to perform, in the offering process, offering to the player at one time a plurality of the game contents;

in the judging process, judging whether not each of the plurality of the game contents is to be made the game content owned by the player by comparing each attribute information of the plurality of the game contents offered at one time to the specified attribute information; and in the combining process, creating a combined game content by combining with an other game content, the game content that is not to be made the game content owned by the player among the plurality of the game contents offered at one time.

According to such a game program, since the other game content after automatic composition is owned by the player even when a plurality of game contents are offered at one time, the time and effort for performing a manipulated input can be saved.

Further, in an information processing device allowing a player to play a game using a game content to which attribute information is set, the information processing device including a registering unit that registers in advance attribute information specified by the player;

an offering unit that offers to the player the game content;

a judging unit that judges whether or not the game content offered is to be made the game content owned by the player, by comparing the attribute information of the game content offered to the specified attribute information;

a combining unit that combines the game content offered with an other game content to create a combined game content when the game content offered is judged not to be made the game content owned by the player; and a recording unit that records the combined game content as the game content owned by the player without recording the game content offered as the game content owned by the player.

According to such a game program, time and effort for performing a manipulated input can be saved.

Present Embodiment

Configuration of Game System 1

FIG. 1 is an example of an overall configuration of a game system 1 according to the present embodiment. The game system 1 according to the present embodiment provides various types of services related to games to a player over a network 2 (for example, the Internet). And the game system 1 includes a server device 10 and a plurality of player terminals 20.

Configuration of Server Device 10

Figure 2:
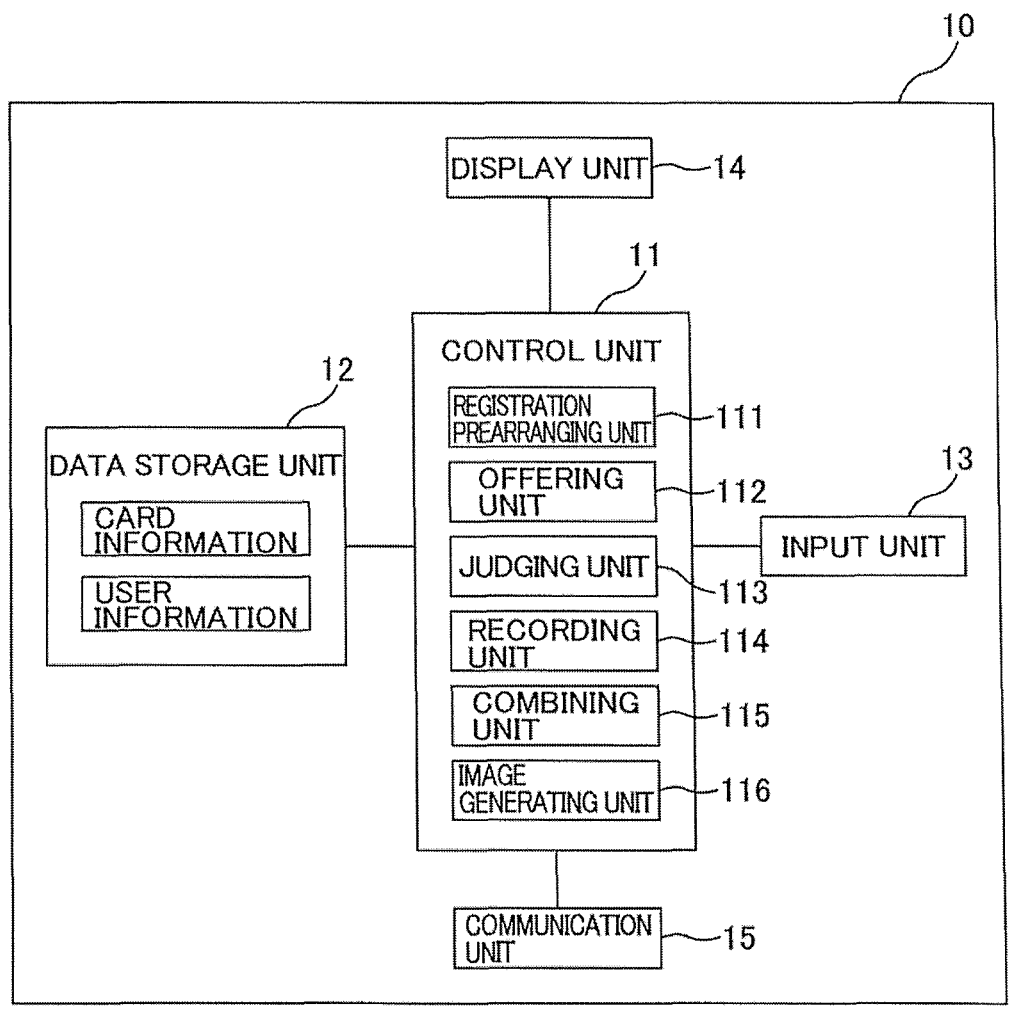
FIG. 2 is a block diagram of a functional configuration of a server device 10.

FIG. 2 is a block diagram of a functional configuration of a server device 10 according to the present embodiment. The server device 10 is an information processing device (for example, workstations, personal computers and etc.) used by the system administrator and the like when operating and managing game services, and can deliver game programs operable on the player terminal 20 and Web pages and the like created in markup languages (HTML etc.) that comply with the standards of the player terminal 20, upon reception of various commands (requests) from the player terminal 20. The server device 10 includes a control unit 11, a data storage unit 12, an input unit 13, a display unit 14, and a communication unit 15.

The control unit 11 is a unit that transfers data among the units and controls the entire server device 10, and is implemented by a central processing unit (CPU) executing a program stored in a certain memory. The control unit 11 according to the present embodiment includes a registration prearranging unit 111, an offering unit 112, a judging unit 113, a recording unit 114, combining unit 115, and an image generating unit 116.

The registration prearranging unit 111 is connected to the data storage unit 12 over the bus and has a function to perform a process for recording, data for prearranging registration, to the data storage unit in response to a command from the control unit 11.

The offering unit 112 has a function to perform a process for offering a game content used in a game to a player. A game content refers to, for example, a game card, a figure and the like that are associated with a character and the like or items and the like such as a tool, ability and the like that can be used in a game.

The judging unit 113 has a function to perform various process for judging, for example, whether or not a game content offered by the offering unit 112 is to be owned by a user.

The recording unit 114 is connected to the data storage unit 12 over the bus and has a function to perform a process for recording data into the data storage unit 12 in response to a command from the control unit 11.

The combining unit 115 has a function to perform a process for creating a game content by composing a plurality of game contents.

The image generating unit 116 has a function to perform a process for generating various image data such as an operation image and a game image for allowing the player to play a game.

The data storage unit 12 has a read only memory (ROM) and a random access memory (RAM): the ROM is a read-only storage region in which system programs are stored, and the RAM is a rewritable storage region which is used as a work area for computing processes performed by the control unit 11. The data storage unit 12 is realized, for example, by a non-volatile storage device such as a flash memory or a hard disk and the like. The data storage unit 12 according to the present embodiment stores card information and player information: the card information is information related to a game card as an example of a game content and the player information is information related to the player. These pieces of information will be described later in detail.

The input unit 13 is a unit with which a system administrator, etc. inputs various types of data (for example, card information and the like), and is realized by, for example, a keyboard a mouse, and the like.

The display unit 14 is a unit which displays operating screens for the system administrator according to commands from the control unit 11, and is realized, for example, by a liquid crystal display (LCD) and the like.

The communication unit 15 is a unit for performing communication between the player terminals 20, and has a function as a reception unit for receiving signals and various data transmitted from the player terminals 20, and a function as a transmission unit for transmitting the signals and various data to the player terminals 20 in accordance with commands from the control unit 11. The communication unit 15 is realized, for example, by a network interface card (NIC) and the like.

Configuration of Player Terminal 20

Figure 3:
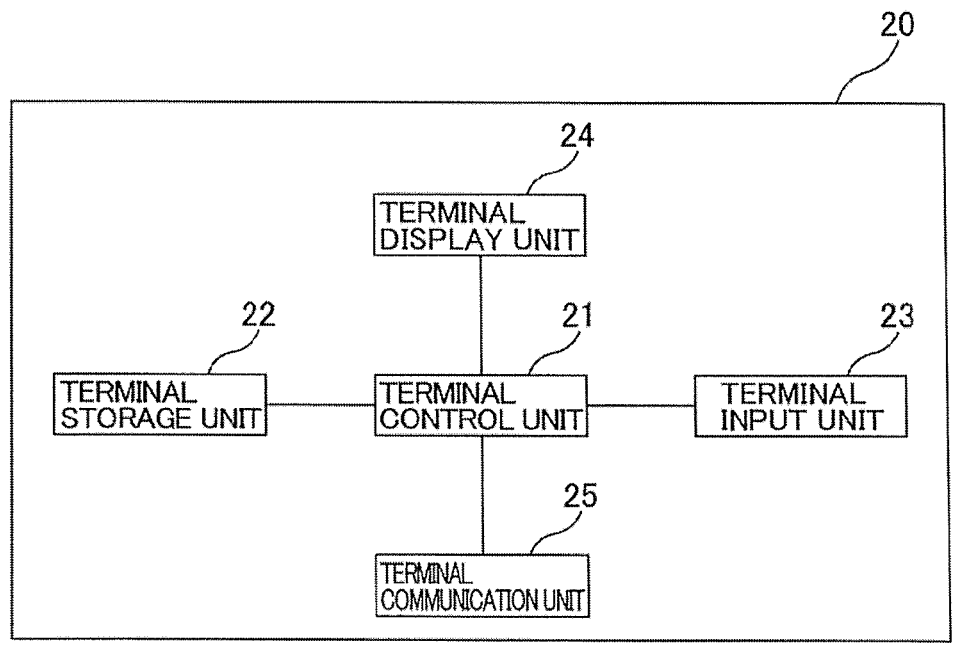
FIG. 3 is a block diagram of a functional configuration of a player terminal 20.

FIG. 3 is a block diagram of a functional configuration of a player terminal 20. The player terminal 20 of the present embodiment is an information processing device (for example, a mobile telephone terminal, a smartphone etc.) used by a player when playing a game and can make a request to the server device 10 to have various information (game programs, Web pages etc.) relating to games delivered. Since the player terminal 20 has a Web browser function for allowing the player to browse Web pages, the player terminal 20 can display Web pages (game play images etc.) distributed from the server device 10 on the screen. The player terminal 20 includes a terminal control unit 21, a terminal storage unit 22, a terminal input unit 23, a terminal display unit 24, and a terminal communication unit 25.

The terminal control unit 21 is a unit that transfers data among the units and controls the entire player terminal 20. The terminal control unit 21 is realized by a central processing unit (CPU) executing a program stored in a certain memory. The terminal control unit 21 of the present embodiment also functions as an image display control unit for controlling the display state of the game screen displayed on the terminal display unit 24.

The terminal storage unit 22 is connected to the terminal control unit 21 through a bus. In accordance with commands from the terminal control unit 21, processes are performed for the data stored in the terminal storage unit 22 to be looked up, read, and rewritten. The terminal storage unit 22 is realized by, for example, a flash memory, a hard disk and the like.

The terminal input unit 23 is a unit with which the player performs various operations (game operations and the like), and is realized, for example, by an operating button, a touchscreen or the like.

The terminal display unit 24 is a unit for displaying a game screen (game image, operation image and the like) according to commands from the terminal control unit 21, and is realized, for example, by a liquid crystal display (LCD) and the like.

The terminal communication unit 25 is a unit that functions as a transmission and receiving unit for transmitting and receiving various information from the server device 10 over the network 2. The terminal communication unit 25 is realized, for example, by a network interface card (NIC) and the like.

Data Structure

FIG. 4 illustrates an example of a data structure of card information stored in the data storage unit 12 of the server device 10. This card information includes items (fields) of card ID, character name, character image, rarity, initial attack power, initial defense power and the like. A card ID is identification information for identifying a game card as one example of a game content. A character name is information that indicates the name of the character named to each type of character to be displayed. In the present embodiment, for example, such as "Warrior A" and "Warrior B" are set to warrior characters and such as "Wizard Z" are set to wizard characters. Specifically, game cards having "0" for the third digit from the right of the card ID have set warrior characters. And cards having "5" for the third digit from the right of the card ID have set wizard characters. The character image is image data of the character. Rarity is a parameter that indicates how rare the character is. Four levels of rarity ("common"→"uncommon"→"rare"→"super rare") are set to the character (game card) in the present embodiment. Specifically, the game card having "1" at the first digit from the right of the card ID is set as "common". The game card having "2" at the first digit from the right of the card ID is set as "uncommon". The game card having "3" at the first digit from the right of the card ID is set as "rare". The game card having "4" at the first digit from the right of the card ID is set as "super rare". The attack power, defense power and the like of the character are parameters that indicate the skill value set to the character.

FIG. 5 shows an example of a table of data configuration of player information stored in the data storage unit 12 of the server device 10. This player information includes items of player ID; friend player ID; virtual currency; play point; owned card information; pictorial book information; and the like. The player ID is identification information for identifying players. The friend player ID is information indicative of other players registered in the player's friend list. Virtual currency is information indicative of the amount of virtual currency owned by the player and is updated such as when the player has consumed the virtual currency. Play point is information indicative of the amount of play points owned by the player and is updated such as when the player has consumed the play points. Owned card information is information indicative of game cards owned by the player (hereinafter also called owned card). Pictorial book information is history information indicative of history of the owned cards that have ever been owned by the player.

FIG. 6 illustrates an example of a data structure of owned card information. This owned card information includes items of owned card ID; level of owned card; attack power; defense power; acquisition dates and times; and the like. The owned card ID is identification information for identifying owned cards. The level of the owned card, attack power, defense power are parameters indicative of skill values set for the character corresponding to the owned card. These various parameters are updated in response to such as the outcome of the battle game. The acquisition date and time is information indicative of date and time the owned card was acquired by the player.

FIG. 7 illustrates an example of a data structure of pictorial book information. This pictorial book information includes items of card ID; flag information; and the like. The card ID is identification information for identifying owned cards that have ever been owned by the player. In the flag information, "true" is set to the card ID of the game card that has ever been owned and "false" is set to the card ID of the game card that has never been owned.

Game Outline

Here, an outline of the game provided by the game system 1 of the present embodiment is described. The game system 1 provides a battle game that is played using game cards (virtual cards used in a virtual space in the game).

Battle Game

In the game system 1 of the present embodiment, the player can own a plurality of game cards having game characters associated thereto. The player can play a battle game using a game card (character) selected from a plurality of game cards owned by the player. The control unit 11 determines the enemy character for battling with the character selected by the player and based on the various parameters (attack power, defense power, hit points and life etc.) set to the various characters, determines the outcome of the battle between these characters.

Offering Game Cards

In the game system 1 of the present embodiment, game cards are offered to the player when the player wins a battle game between an enemy character or when playing a random selection game so-called "Gacha Gacha" (registered trademark).

This random selection game is a game where a game card selected from a plurality of game cards is offered to the player. In this random selection game, an ordinary random selection game and a special random selection game are played. The ordinary random selection game is a game where one game card is offered to the player for one random selection. The special random selection game is a game where a plurality of game cards is offered to the player for one random selection. The player can selectively play the ordinary random selection game and the special random selection game.

The player can increase the number of owned cards owned by the player up to the limit by owning game cards offered (also called offered card) by such as a random selection game in the above manner. And the player can play the aforementioned battle game using the owned card owned by the player. Further, as will be described later, the player can combine game cards using owned cards owned by the player.

Game Card Combination

In the game system 1 of the present embodiment, the player can create a game card (combine a game card) by organizing a plurality of game cards. Various parameters (e.g., level, attack power, defense power etc.) of the character associated with the character of the combined game card changes with the combination of game cards.

In the present embodiment, a game card is combined by organizing at least one material card with a base card. The values of the parameters such as level, attack power, defense power set to the card before combination increases by organizing the game cards, and the new increased parameter is set to the combined base card. The player will own only the combined base card without owning both the base card and the material card when game cards are combined in such manner.

Further, in the present embodiment, game cards can be automatically combined without a player's manipulated input by prearranged registration of the game cards used for card combination. Thus, time and effort required for performing a manipulated input can be relieved since, when a game card is offered to the player, the offered game card is automatically judged whether or not the offered game card is to be owned by the player and then combined.

Operation of Game System 1

Figure 8:
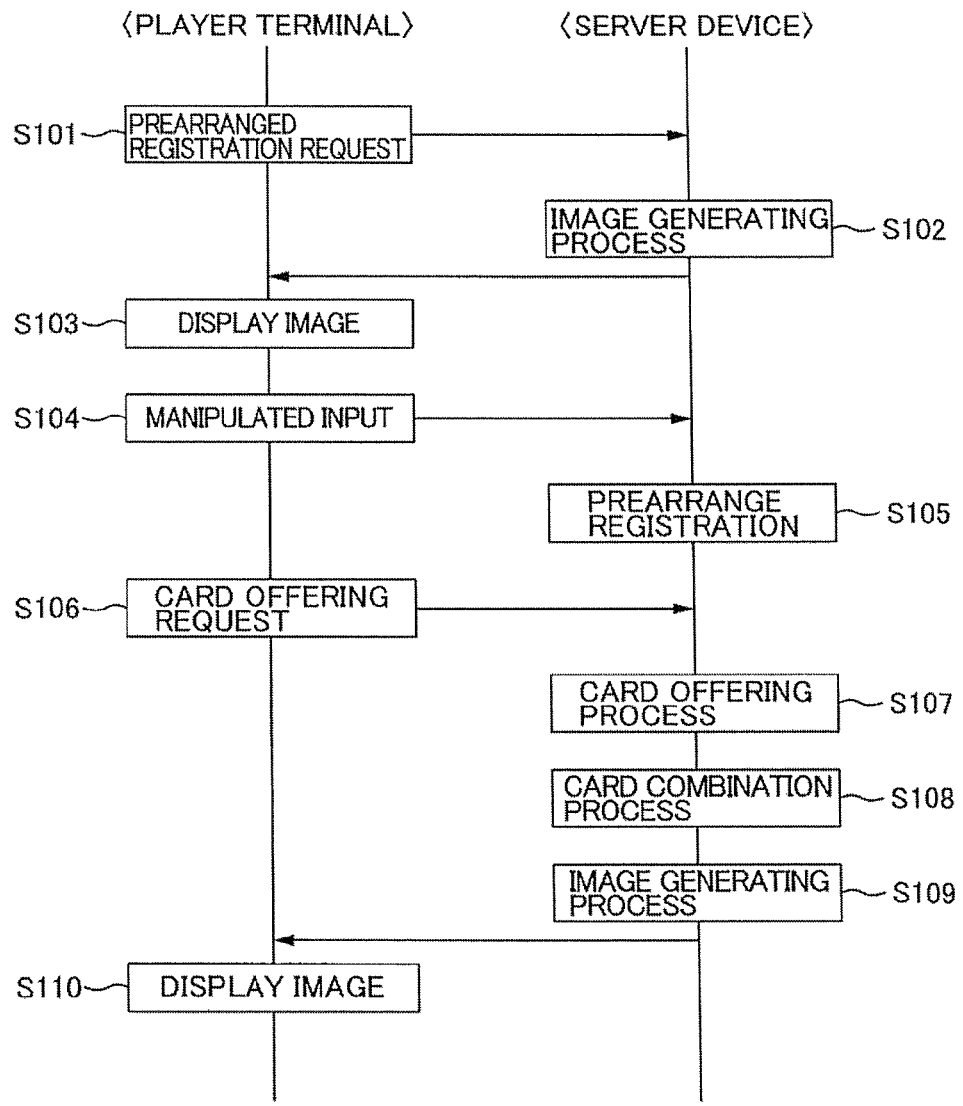
FIG. 8 is a flowchart describing an operation example of the game system 1.

FIG. 8 illustrates a flow chart explaining an operation example relating to combination of game cards in the game system 1.

First, in the player terminal 20, when the terminal control unit 21 receives a manipulated input from the terminal input unit 23 to start prearranged registration from the player, a command for starting prearranged registration (prearranged registration request) is sent through the terminal communication unit 25 to the server device 10 (S101).

Next, when receiving a prearranged registration request sent from the player terminal 20, the server device 10 sends a game image (image data) generated by the image generating unit 116 through the communication unit 15 to the player terminal 20 of the requestor (S102).

Then the player terminal 20 displays the game screen on the terminal display unit 24 based on the game image (image data) sent from the server device 10 (S103).

Figure 9:
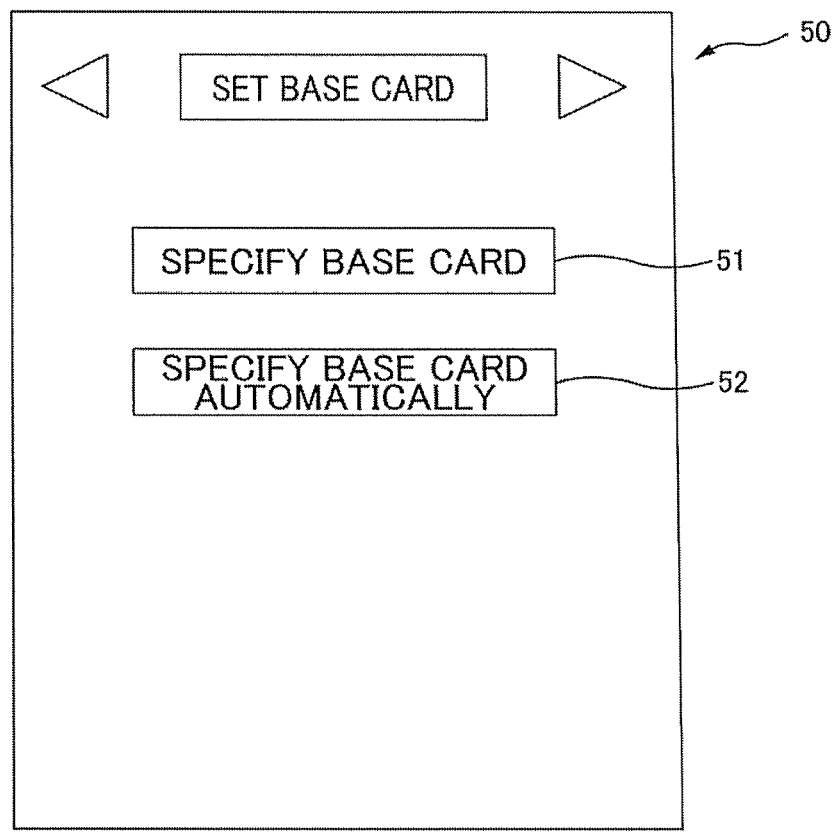
FIG. 9 illustrates an example of a game screen when setting a base card.

FIG. 9 illustrates an example of a game screen for setting a base card displayed on this terminal display unit 24. The game screen 50 is a game screen for making the player perform a manipulated input relating to the setting of the base card and includes a specify base card button 51 and a specify base card automatically button 52. When the specify base card button 51 is selected by the player, the game screen changes to that for prearranged registration of the base card specified by the player himself/herself (see FIG. 10). Further, when the specify base card automatically button 52 is selected by the player, the game screen changes to that for the player to input the conditions for specification when the base card is automatically specified (see FIG. 11).

Figure 10:
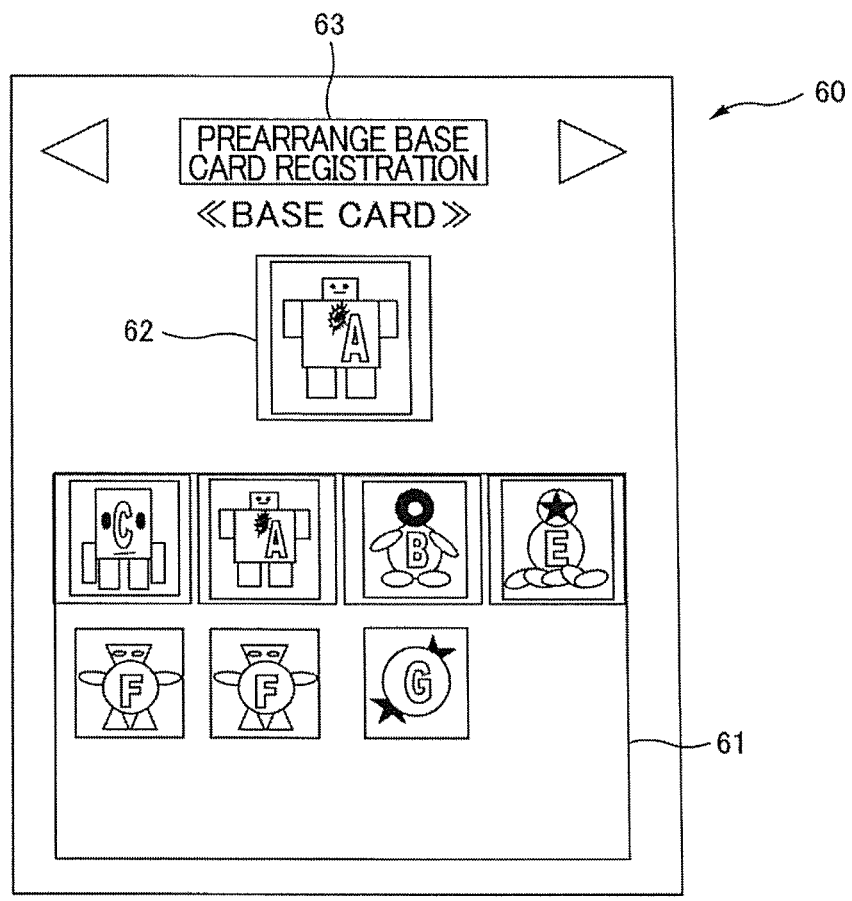
FIG. 10 illustrates an example of a game screen when specifying a base card.

The game screen 60 shown in FIG. 10 includes an owned card area 61, a base card area 62 and a prearrange base card registration button 63. When any one game card is selected from the plurality of game cards displayed on the owned card area 61 by a player's manipulated input, the selected game card is displayed in the base card area 62 as the base card. And when the prearrange base card registration button 63 is selected by the player, prearranged registration of the base card displayed in the base card area 62 is started.

Figure 11:
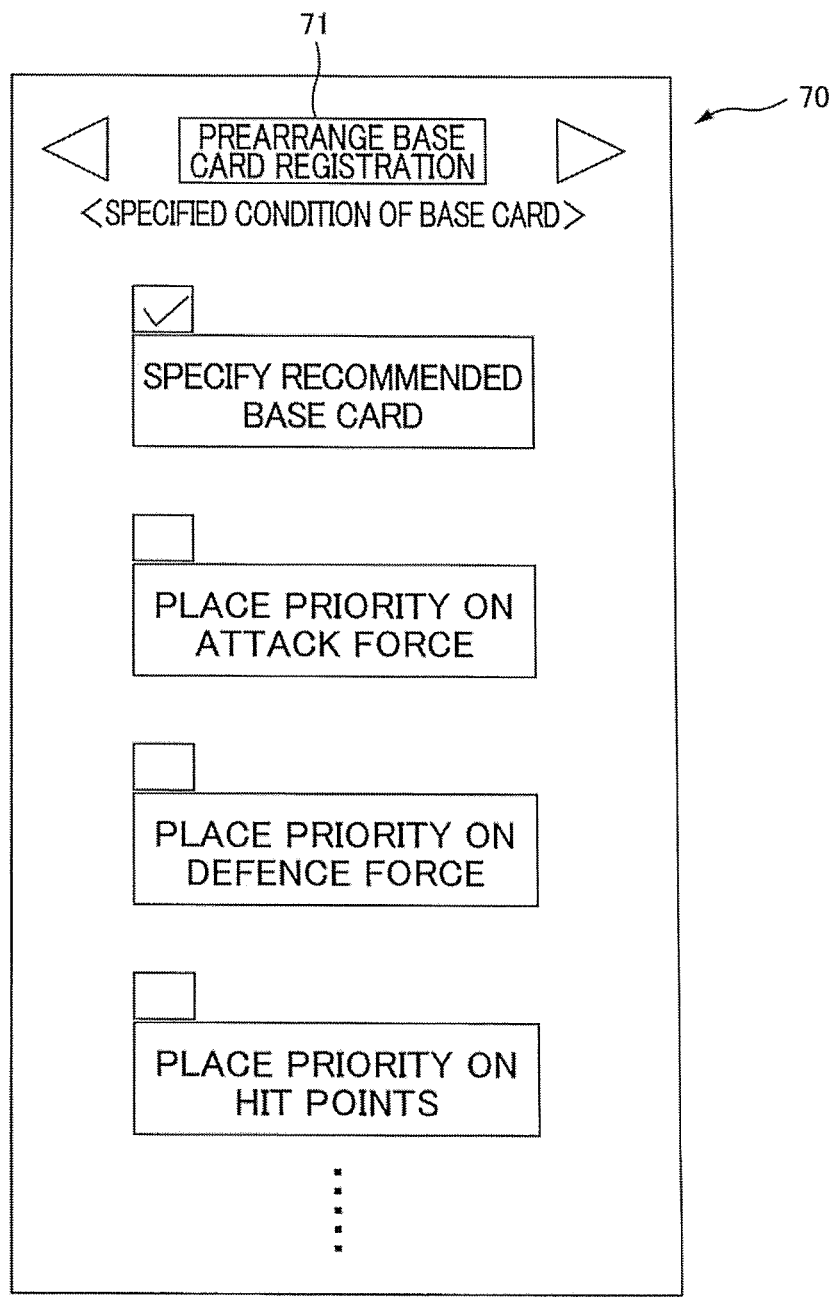
FIG. 11 illustrates an example of a game screen when inputting a specific condition of a base card.

Meanwhile, the game screen 70 illustrated in FIG. 11 displays a prearrange base card registration button 71 and a plurality of conditions for specification used when abase card is automatically specified, as well. When any one of the check boxes of the conditions for specification is selected by the player's manipulated input, and the prearrange base card registration button 71 is selected, prearranged registration of the base card automatically specified based on the selected condition for specification is started.

Figure 12:
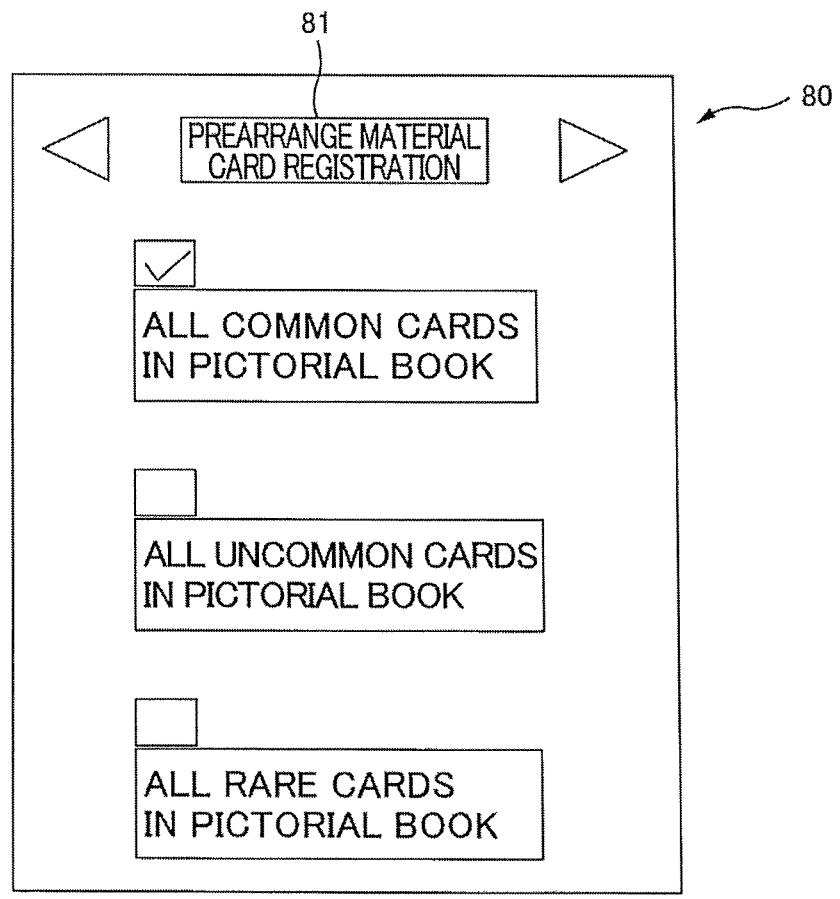
FIG. 12 illustrates an example of a game screen when performing prearranged registration of a material card.

FIG. 12 illustrates an example of the game screen for prearranged registration of a material card, displayed on this terminal display unit 24. The game screen 80 is a game screen for prearranged registration of the attribute information specified by the player himself/herself and displays prearrange material card registration button 81 as well as a plurality of rarities as an example of attribute information set to the material card. Any one of the rarities is specified by the player's manipulated input and prearranged registration of the specified rarity starts when the prearrange material card registration button 81 is selected.

Returning to FIG. 8, when operation information relating to prearranged registration of the base card and the material card are input by the player in the above manner, this operation information is sent from the player terminal 20 to the server device 10 (S104).

Then the server device 10 performs prearranged registration for the base card and the material card based on operation information received from the player terminal 20 (S105). Specifically, when the base card is specified by the player in the game screen 60 shown in FIG. 10, the registration prearranging unit 111 registers in the data storage unit 12 in advance the base card specified by the player himself/herself. And when the check box for "specify recommended base card" is selected by the player in the game screen 70 shown in FIG. 11, or when a prearranged registration is not requested by the player, the registration prearranging unit 111 refers to the owned card information shown in FIG. 6 and registers in the data storage unit 12 in advance as a base card, a game card specified from the player's owned cards without a player's manipulated input. For example, the game card (the game card with the highest level of attack power, the game card with the highest level of rarity, etc.) most appropriate to the situation of the game is automatically specified as the base card. And when "place priority on attack force" is selected by the player in the game screen 70 shown in FIG. 11, the registration prearranging unit 111 refers to the owned card information shown in FIG. 6 and registers in advance in the data storage unit 12, as a base card a specified game card among the player's owned cards by placing priority on the level of attack power. For example, the game card currently having the largest attack parameter value, the game card having the largest attack parameter value when having the level of the game card increased to maximum, and the like are automatically specified as the base card. And when the rarity of the material card is specified in the game screen 80 shown in FIG. 12 by the player, the registration prearranging unit 111 registers in advance in the data storage unit 12 the rarity specified by the player himself/herself.

Here, in the player terminal 20, when the terminal control unit 21 receives a player's manipulated input to start card offering from the terminal input unit 23, the terminal control unit 21 sends a command (card offering request) to start card offering through the terminal communication unit 25 to the server device 10 (S106).

Then upon reception of a card offering request sent from the player terminal 20, the server device 10 performs the card offering process for offering a game card to the player (S107). In the present embodiment, game cards are offered to the player by playing battle games or random selection games.

In the case of a battle game, the offering unit 112 of the server device 10 performs a game process relating to a battle game and determines the contents and the outcome of the battle. Then based on the contents and the outcome of the battle, the offering unit 112 refers to the card information shown in FIG. 4 and offers the game cards selected from the plurality of game cards to the player.

In the case of a random selection game, the offering unit 112 performs a game process relating to a random selection game and refers to the card information shown in FIG. 4 to offer to the player game cards selected from a plurality of game cards using random numbers. The offering unit 112 offers one game card for a single random selection in a normal random selection game and offers 10 game cards for a single random selection in a special random selection game.

Subsequently, when game cards are offered to the player by this card offering process, the server device 10 judges whether the offered game cards are to be made the player's owned game cards and performs a card combination process for combining game cards based on the judgment result (S108).

Figure 13:
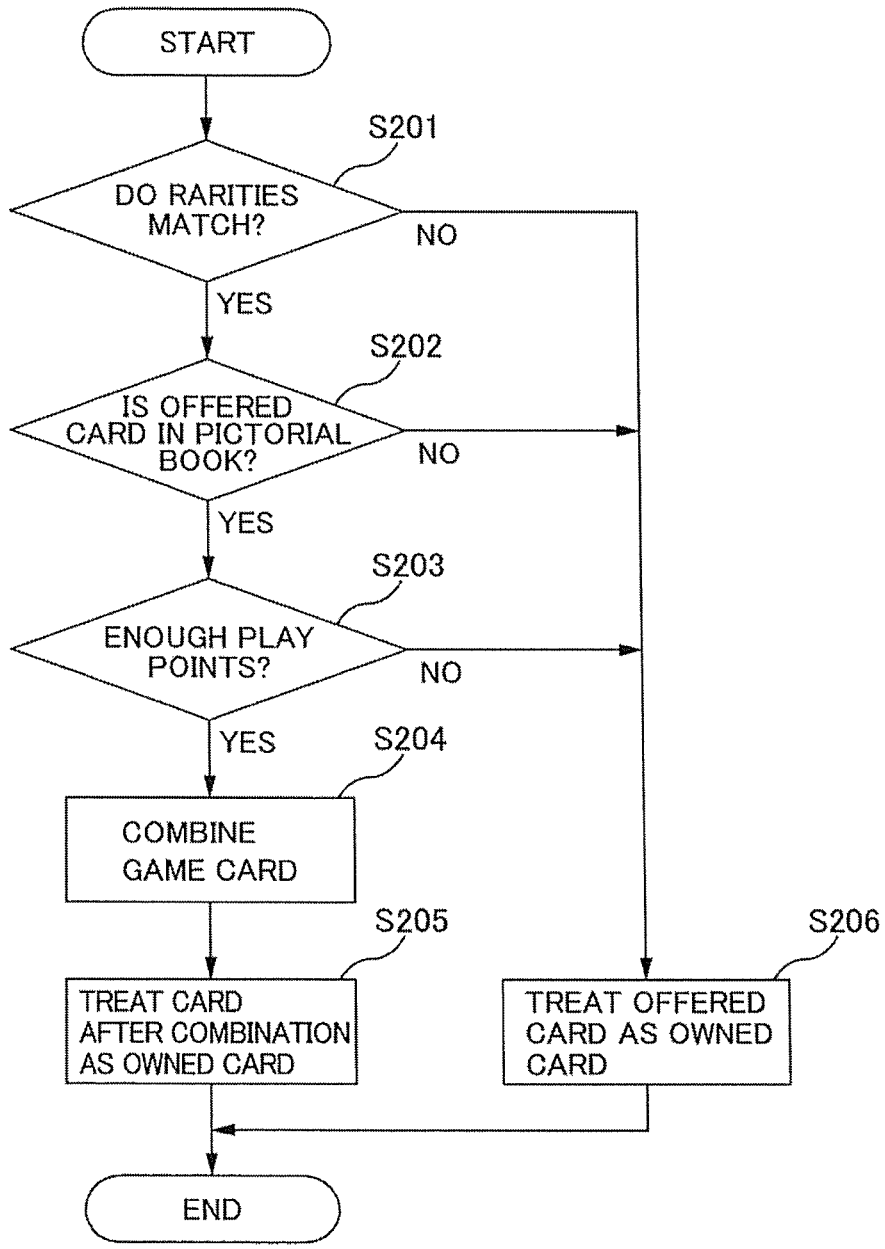
FIG. 13 is a flowchart describing a card composition process.

FIG. 13 is a flow chart illustrating the card combination process.

First, the judging unit 113 in the server device 10 compares the rarity of the offered card offered to the player by the card offering process to the rarity specified by the player in prearranged registration to judge whether the offered card is to be made an owned card to be owned by the player (S201).

Note that when a plurality of game cards are offered to the player at one time by the card offering process, the judging unit 113 compares each of the offered cards to the rarity specified by the player in prearranged registration for judgment.

Specifically, the judgment unit 113 in the present embodiment judges whether or not the rarity of the offered card and the rarity specified by the player match. When the judgment unit 113 judges that the rarities match (S201: YES), the process proceeds to the subsequent step S202. On the other hand, when the judgment unit 113 unit judges that the rarities do not match (S201: NO), the judgment unit 113 sets the offered card as the player's owned card (S206). At this time, the recording unit 114 updates the player's owned card information (see FIG. 6) by adding a record of the offered card as the player's owned card in the data storage unit 12.

In step 202, when the rarities match (S201: YES), the judging unit 113 judges whether or not the card ID of the offered card matches the card ID (set "TRUE") included in the pictorial information (see FIG. 7). When the card IDs match (S202: YES), the judging unit 113 proceeds to the subsequent step S203. On the other hand, when the judging unit 113 judges that the card IDs do not match (S202: NO), the judging unit sets the offered card as the player's owned card (S206). At this time, the recording unit 114 adds the offered card to the player's owned card information (see FIG. 6) and updates the record.

In step S203, when the card IDs match (S202: YES), the judging unit 113 refers to the player information shown in FIG. 5 and judges whether or not the player's play points is equal to or greater than a predetermined number of points. When the play points is equal to or greater than the predetermined number of points (S203: YES), the judging unit 113 consumes a predetermined number of points from the play points owned by the player (automatically updates the player information shown in FIG. 5) and proceeds to the subsequent step S204. On the other hand, when the play points are lacking (S203: NO), the judging unit 113 sets the offered card as the player's owned card (S206). At this time, the recording unit 114 adds the offered card to the player's owned card information (see FIG. 6) and updates the record.

In step S204, when there are enough play points (S203), the judging unit 113 combines game cards by organizing with the base card the offered card as the material card.

Specifically, when the player himself/herself is specifying the base card in the game screen 60 shown in FIG. 10, the combining unit 115 of the server device 10 reads the base card (the base card specified by the player) registered in the data storage unit 12 in advance and then organizes an offered card as the material card with the base card. Further, when the "specify recommended base card" is selected by the player in the game screen 70 shown in FIG. 11, the combining unit 115 reads the base card (the base card a game card automatically specified without a player's manipulated input) registered in the data storage unit 12 in advance and then organizes an offered card as the material card with the base card. Further, when each of the specifying conditions other than "specify recommended base card" is selected by the player in the game screen 70 shown in FIG. 11, the combining unit 115 reads the base card (the base card automatically specified without a player's manipulated input, based on each of the specifying conditions specified by the player) registered in the data storage unit 12 in advance, and then organizes an offered card as the material card with the base card.

Note that when a plurality of game cards are offered to the player at one time by the card offering process, a game card is combined by the combining unit 115 organizing with the base card a plurality of offered cards as the material cards.

When a material card is organized with a base card in this way, the combining unit 115 refers to the owned card information shown in FIG. 6 and acquires the capability parameters such as level, attack power, defense power and the like of the base card, and increases the acquired capability values to update to a new capability parameter. Then the combining unit 115 sets the base card having the new increased capability parameter as the combined base card.

Subsequently, when the came card is combined in this way, the offered card (material card) is not recorded in the data storage unit 12 as the player's owned card but the combined base card is recorded in the data storage unit 12 as the player's owned card (S205). In other words, the recording unit 114 in the server device 10 updates the record of the owned card information shown in FIG. 5 and resets the combined base card as the player's owned card.

Returning to FIG. 8, when a game card is combined by such card combination process, the server device 10 sends the game image (image data) generated by the image generating unit 116 through the communication unit 15 to the player terminal 20 being the request source (S109).

Subsequently, the player terminal 20 displays the game screen on the terminal display unit 24 based on the game image (image data) sent from the server device 10 (S110). The player can confirm that the offered card as a material card has been automatically combined with the base card, the offered card has been added as the player's owned card and the like by looking at the game screen displayed on the terminal display unit 24.

As explained above, according to the game system 1 of the present embodiment, a combined game card can be created by automatically organizing with a base card an offered card, as a material card, with the same rarity as the rarity registered in advance, when a game card is offered to the player. For example, as long as the player makes a prearranged registration of a low rarity, a card will be automatically combined with the base card even when the card is an offered card with a low rarity value, so that an operation for discarding or selling the card with a low rarity value is not required. Therefore, time and effort required for manipulated input can be relieved.

Other Embodiments

The aforementioned embodiment is for facilitating the understanding of the present invention and is not intended to limit the interpretation of the present invention. Variations and modifications may be made within the spirit and scope of the present invention and equivalents thereof are included in the present invention. In particular, embodiments described below are included in the present invention.

Card Combination Process

In the aforementioned embodiment, when a special random selection game was performed in the card offering process (S107) shown in FIG. 8 and a plurality of game cards were offered to the player at one time, a plurality of offered cards as material cards may be organized with the base card in the card combination process (S108) shown in FIG. 8. At this time, a part of the offer cards among the plurality of offer cards may be used for game card combination, and the remaining offered cards among the plurality of offered cards may be owned by the player. For example, when there are eight material cards in the plurality of offer cards, a material card is organized with a base card (for example six material cards) until the level of the combined base card reaches the maximum value, and the remaining two material cards are made the player's owned card.

Additionally, in the aforementioned embodiment, an example was given to describe a case where judgment processes S201 to S203 were performed in the card combination process shown in FIG. 13, however, the present invention is not limited to such. For example, the judgment unit 113 may be made to perform only step S201 and omit steps S202 and S203. That is, judgment on matching of rarity may only be performed.

Further, in the aforementioned embodiment, description was made giving an example of a case where a material card whose rarity matches the rarity specified by the player himself/herself was combined with the base card, however, the invention is not limited to such and a material card whose rarity does not match the rarity specified by the player himself/herself may be combined with the base card. For example, the player specifies a super rare or a rare for prearranged registration, and when the offered game card is a common card, the common card is combined with a base card since the rarities of the two do not match.

Furthermore, in the aforementioned embodiment, combination is not limited to a case where a single base card is organized with a single material card and two or more material cards may be organized for combination. Additionally, combination where a plurality of material cards of the same type and a plurality of material cards of different types can be organized with a base card. For example, a game card may be combined by organizing three material cards of the same type and two material cards of a different type with a base card (by organizing a total of six game cards).

Card Offering Process

In the aforementioned embodiment, description was given taking a battle game and a random selection game as one example of the card offering process, however, the present invention is not limited to such. For example, a game card may be offered by the player conquering a mission given to the player. Further, a game card may be offered by the player inputting a serial code displayed on a Web page and the like. Furthermore, a game card may be offered by the player logging into the game system 1. Still furthermore, a game card may be offered through an event (consuming points in an event, those ranked at the top) provided in the game system 1.

Specification of Base Card

In the aforementioned embodiment, description was given taking an example where a base card was set with a game card specified among the owned cards when base cards are automatically specified without the player's operation (for example, when "specify recommended base card" is selected in the game screen 70 shown in FIG. 11), however, the present invention is not limited to such. For example, a base card may be automatically specified from a plurality of offered game cards when a special random selection game is played in the card offering process (S107) shown in FIG. 8 and a plurality of game cards are offered to the player at one time.

Prearranged Registration of Material Cards

In the aforementioned embodiment, description was given taking the game screen shown in FIG. 12 as an example of a game screen for prearranged registration of a material card, however, the present invention is not limited to such. For example, the game screen shown in FIG. 14 may be used as the game screen for prearranged registration of a material card. The game screen 90 is a game screen for prearranged registration of attribute information specified by the player himself/herself, and the pull-down menu 91 and the prearrange material card registration button 92 is displayed as well as a plurality of rarities is displayed as an example of attribute information set to the material card. The pull-down menu 91 includes three selection items of "not selected", "sell", and "combine". The player operates the pull-down menu 91 to specify "combine" for each rarity ("common", "uncommon", and "rare") and thereafter performs prearranged registration for each rarity by selecting the prearrange material card registration button 92. In the game screen shown in FIG. 14, "combine" is specified for "uncommon" by the player. In this way, the registration prearranging unit 111 registers in the data storage unit 12 in advance "uncommon" specified by the player himself/herself as data used at the time of organizing the material card.

Note that, the registration prearranging unit 111 can register "common" in the data storage unit 12 in advance as data used at the time of selling the offered card. When selling the offered card, processes of automatically selling the offered card without a player's operation and offering of a play point to the player based on the value (rarity, initial attack power, initial defense power of the character, etc.) of the offered card are performed. In the game screen shown in FIG. 14, "sell" is specified for "common" by the player so that the offered card is automatically sold when the rarity of the offered card is "common".

Figure 14:
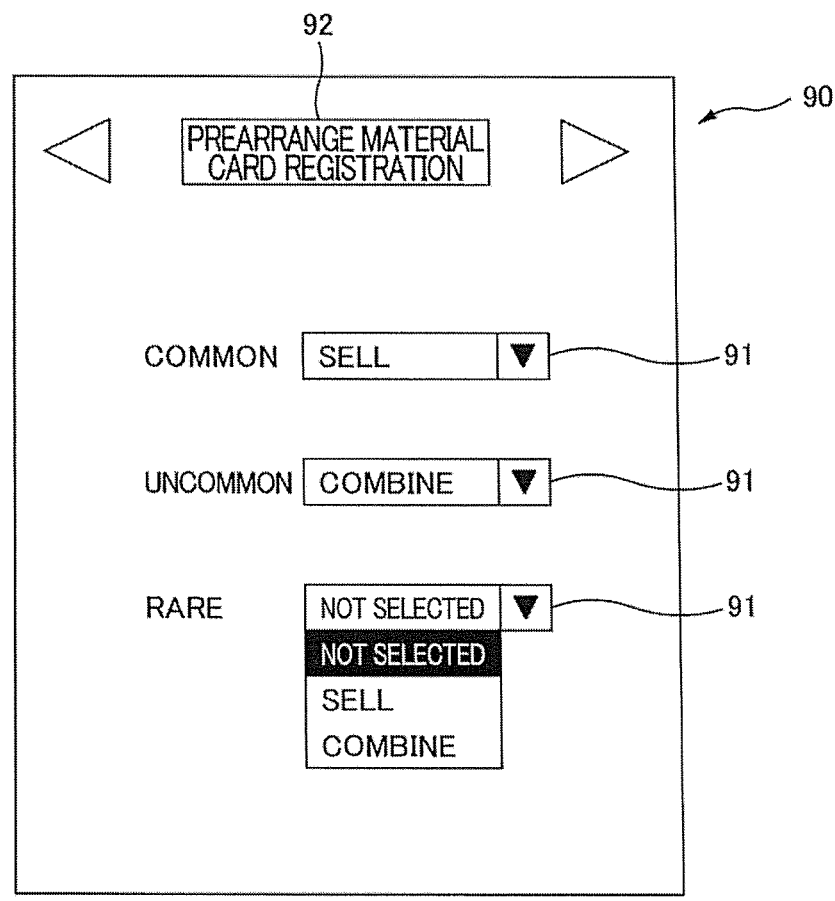
FIG. 14 illustrates another example of a game screen when performing prearranged registration of a material card.

Additionally, in the game screen shown in FIG. 14, "not selected" is specified for "rare" by the player so that the offered card becomes the player's owned card when the rarity of the offered card is "rare".

Server Device

In the aforementioned embodiment, description was given taking the game system 1 including one server device 10 as one example of the server device, however, the invention is not limited to such and the game system 1 can include a plurality of server devices as one example of the server device. In other words, each server device 10 may be made to perform various processes in a distributed manner with a plurality of server devices 10 connected over the network 2.

Information Processing Device

In the game system 1 of the aforementioned embodiment, description was given taking an example where the server device 10 and the player terminals 20 cooperate based on a game program and various information processes such as the card offering process and the card combining process were performed. However, the invention is not limited to such and the player terminal 20 alone or the server device 10 alone, as the information processing device can be made to execute the aforementioned various information processes based on the game program.

Further, a configuration may be employed where a part of the function as the information processing device is performed by the player terminal 20. In this case, the server device 10 and the player terminal 20 configures the information processing device.

Note that, the information processing device is a computer that includes a processor and a memory.

Game Program

In the game system 1 of the aforementioned embodiment, description was given taking an example where various information processes were performed by the server device 10 and the player terminal 20 cooperating with each other. However, the present invention includes a game program for performing these processes. In other words, the server device 10 and the player terminal 20 as the information processing device can be made to perform the aforementioned processes based on a game program.

What is claimed is:

1. A non-transitory computer-readable storage medium storing a game program to be executed by a computer including a processor and a memory, the game program instructing the computer to perform the following processes of:
   a base game content registering process to register a player's base game content in advance in a storage unit, based on a first specifying operation by the player;
   a material game content registering process to register in advance in the storage unit, based on a second specifying operation by the player, in association with each rarity, whether or not a game content having the rarity is made a material game content to be combined with the base game content;
   a game content offering process to offer a game content having rarity to the player;
   a rarity comparing process to compare the rarity of the game content offered to the player in the game content offering process to the rarity of the game content registered in advance as the material game content in the material game content registering process; and
   a game content combining process to combine the game content offered to the player with the base game content as the material game content based on a comparison result in the rarity comparing process, thereby varying a parameter stored in the storage unit in relation to the base game content.

2. A non-transitory computer-readable storage medium storing a game program to be executed by a computer including a processor and a memory, the game program instructing the computer to perform the following processes of:
   a game content sale registering process to register in advance in a storage unit, based on a specifying operation by a player, in association with rarity, whether or not a game content having the rarity is made a target for sale;
   a game content offering process to offer a game content having rarity to the player;
   a rarity comparing process to compare the rarity of the game content offered to the player in the game content offering process to the rarity of the game content registered in advance as the target for sale in the game content sale registering process; and
   a game content selling process to sell the game content offered to the player based on a comparison result in the rarity comparing process, thereby storing game points given according to the value of the game content sold in the storage unit in relation to the player.

3. The computer-readable storage medium according to claim 2, wherein the game program instructs the computer to perform:
   in the game content sale registering process, registering in the storage unit in advance, in association with each rarity, whether or not the game content to which the rarity is set is made the target for sale.

4. An information processing device comprising:
a storage unit which stores a game program; and
a control unit which performs, according to the game program, the following processes of:
  a base game content registering process to register a player's base game content in advance in the storage unit, based on a first specifying operation by the player;
  a material game content registering process to register in advance in the storage unit, based on a second specifying operation by the player, in association with each rarity, whether or not a game content having the rarity is made a material game content to be combined with the base game content;
  a game content offering process to offer a game content having rarity to the player;
  a rarity comparing process to compare the rarity of the game content offered to the player in the game content offering process to the rarity of the game content registered in advance as the material game content in the material game content registering process; and
  a game content combining process to combine the game content offered to the player with the base game content as the material game content based on a comparison result in the rarity comparing process, thereby varying a parameter stored in the storage unit in relation to the base game content.

5. An information processing device comprising:
a storage unit which stores a game program; and
a control unit which performs, according to the game program, the following processes of:
  a game content sale registering process to register in advance in the storage unit, based on a specifying operation by a player, in association with rarity, whether or not a game content having the rarity is made a target for sale;
  a game content offering process to offer a game content having rarity to the player;
  a rarity comparing process to compare the rarity of the game content offered to the player in the game content offering process to the rarity of the game content registered in advance as the target for sale in the game content sale registering process; and
  a game content selling process to sell the game content offered to the player based on a comparison result in the rarity comparing process, thereby storing game points given according to the value of the game content sold in the storage unit in relation to the player.

* * * * *